US006893880B2

(12) United States Patent
Carpenter

(10) Patent No.: US 6,893,880 B2
(45) Date of Patent: *May 17, 2005

(54) ANALYTE ASSAYS AND DEVICES

(75) Inventor: Charles Carpenter, Scarborough, ME (US)

(73) Assignee: IDEXX Laboratories, Westbrook, ME (US)

( * ) Notice: Subject to any disclaimer, the term of this patent is extended or adjusted under 35 U.S.C. 154(b) by 340 days.

This patent is subject to a terminal disclaimer.

(21) Appl. No.: 09/843,961

(22) Filed: Apr. 27, 2001

(65) Prior Publication Data

US 2001/0016360 A1 Aug. 23, 2001

Related U.S. Application Data

(63) Continuation of application No. 09/105,822, filed on Jun. 26, 1998, now Pat. No. 6,235,539, which is a continuation-in-part of application No. 08/736,801, filed on Oct. 25, 1996, now abandoned.

(51) Int. Cl.$^7$ ................................................ G01N 33/53
(52) U.S. Cl. ........................ 436/514; 436/524; 436/810; 436/518; 435/7.1; 435/287.7; 435/288.1; 435/288.2; 435/970; 422/56; 422/58
(58) Field of Search ................................. 436/518, 524, 436/530, 541, 807, 514, 810; 435/7.1, 7.93, 7.94, 287.7, 287.9, 288.7, 970, 288.1, 288.2; 422/56, 58, 99, 104, 59, 60

(56) References Cited

U.S. PATENT DOCUMENTS

| 4,624,929 A | * | 11/1986 | Ullman ........................ 436/179 |
| 4,734,360 A | | 3/1988 | Phillips ........................ 435/25 |
| 4,735,203 A | | 4/1988 | Ryder et al. ................. 128/314 |
| 4,857,453 A | * | 8/1989 | Ullman et al. ............. 435/7.92 |
| 4,978,504 A | | 12/1990 | Nason .......................... 422/61 |
| 5,169,789 A | * | 12/1992 | Bernstein .................... 436/501 |
| 5,415,994 A | * | 5/1995 | Imrich et al. .................. 435/5 |
| 5,624,458 A | | 4/1997 | Lipscher ..................... 606/181 |
| 5,753,497 A | | 5/1998 | Bernstein et al. ......... 435/287.1 |
| 5,795,543 A | | 8/1998 | Poto et al. ................ 422/82.05 |
| 5,877,028 A | * | 3/1999 | Chandler et al. ........... 436/514 |
| 5,908,786 A | | 6/1999 | Moreno et al. ............... 436/69 |
| 5,913,833 A | | 6/1999 | Elstrom et al. ............. 600/573 |
| 6,140,136 A | * | 10/2000 | Lee ............................. 436/518 |

FOREIGN PATENT DOCUMENTS

| EP | 183 442 | 6/1986 |
| EP | 306 336 | 4/1989 |
| EP | 582 231 | 2/1994 |
| EP | 679 893 | 11/1995 |
| WO | WO 88/08534 | 11/1988 |
| WO | WO 93/03176 | 2/1993 |
| WO | WO 94/29696 | 12/1994 |
| WO | WO 95/16207 | 6/1995 |

* cited by examiner

*Primary Examiner*—Bao-Thuy L. Nguyen
(74) *Attorney, Agent, or Firm*—McDonnell Boehnen Hulbert & Berghoff

(57) ABSTRACT

The present invention provides a method and a device that utilizes capillarity-mediated, chromatographic transport, for the qualitative or semi-quantitative analysis of selected analytes in liquid samples. The device utilizes an applicator/collection device for collecting and administering the sample to the flow path such that reagent(s) flow through the applicator/collection device, washing the sample into the reaction pathway. The device further utilizes an air gap between the initial location of the reagent and the reaction pathway to funnel the reagent efficiently through the sample so as to collect all or substantially all of the sample and make it available for the reaction(s).

33 Claims, 7 Drawing Sheets

A

B

ANALYTE ASSAYS AND DEVICES

This application is a continuation of application Ser. No. 09/105,822 filed Jun. 26, 1998, now U.S. Pat. No. 6,235,539, which is a continuation-in-part of application Ser. No. 08/736,801, filed Oct. 25, 1996, now abandoned.

FIELD OF INVENTION

The present invention relates to improved analyte assays and devices for quantitative or qualitative assays of a member of any type of binding pair such as ligand-receptor, antigen-antibody, etc., as well as for substrates or products or products of chemical and biochemical reactions. This includes immunometric assays, which are designed for the analysis of selected analyte(s) in a sample.

BACKGROUND OF INVENTION

Today binding-pair assays are utilized extensively in such fields as clinical, forensic, and veterinary medicine, pharmacological testing, environmental monitoring, food quality assurance, and other related areas. All these fields have needs for rapid and effective analysis of specific substances (referred to as analytes), which are frequently found in low concentrations within the given test sample. The basic principles and mechanisms of assays are specifically designed to accommodate such urgent needs.

These assays are especially useful in the in vitro determination of the presence and concentration of analytes within physiological fluids. For example, the determination of specific proteins, enzymes, hormones, metabolites, and therapeutic or toxic drugs within the blood, urine, or cerebral spinal fluid has greatly enhanced the efficacy of diagnostic methodologies in clinical medicine.

Moreover, the development of non-radioactive labeling components, which allow the direct visualization of the completed reaction, has facilitated the use of binding-pair assay procedures outside of the "typical" laboratory. For example, in clinical office settings, non-radioactively-labeled, binding-pair assays are useful for providing rapid, simple procedures which may be performed while the patient is still in the office. Thus diagnosis can be accomplished without delay, and treatment may be instituted during a single visit.

Without such assays, it was frequently necessary to collect the sample from the patient during a first visit and to have the biological sample analyzed by a clinical laboratory at a later time. During such time, the patient was sent home and often required to return for a second office visit in order to receive the proper treatment and/or medication. Such delay was at best inefficient, and at worst potentially life threatening.

The term "binding-pair assay" refers to an assay between two binding-pair members designed to facilitate the formation of a complex between a particular analyte of interest and another substance capable of specific interaction with the analyte. In this way, the presence of particular analyte may be detected. Alternatively, the binding-pair member may be a substance which, if detectable, may be used to infer the presence or absence of the analyte within the sample.

In the context of the present invention, the term "analyte" refers to, but is not limited to, compounds such as proteins, modified proteins, peptides, nucleic acids such as deoxyribonucleic acid (DNA), ribonucleic acid (RNA), peptide nucleic acid (PNA), haptens, antigens, antibodies, and any metabolites of these substances and any other compounds, either natural or synthetic, which may be of diagnostic interest and which have a specific binding partner (e.g., the receptor moiety of a ligand-receptor assay, or the substrate of an enzyme).

Binding-pair assays rely upon the binding of one analyte by its specific binding partner to determine the concentration of the analyte within the test sample. Binding-pair assays may be differentiated and categorized as either competitive or non-competitive in nature. Non-competitive assays generally utilize the receptor component in a substantial excess over the concentration of the analyte to be determined in the assay.

One type of non-competitive assay is usually referred to as "sandwich assay." It employs the methodology whereby the analyte is detected via its binding to two binding partners. One partner may be labeled to facilitate a subsequent detection and the other is immobilized to a solid-phase to facilitate separation of the bound analytes from unbound reaction components (e.g., unbound labeled first receptor). An alternate non-competitive assay can be termed a "blocking assay." In this type of assay, sample is first mixed with a binding partner (usually labeled), and any analyte in the sample binds to the binding partner. The mixture is then allowed to react with analyte analog, which is usually bound to a solid phase. The more analyte is present in the sample, the more binding sites on the binding partner will be blocked, and the less sites there will be for the analyte analog to bind. Thus, in this form of assay, the more label is bound to the solid phase, the less analyte is present in the test sample.

In contrast, competitive binding-pair assays generally involve analyte from the test sample, a purified binding partner or binding partner analog that is labeled to facilitate detection, and a rate-limiting concentration of binding-partner species. The sample analyte and the labeled analyte/analyte analog moieties are subsequently allowed to compete for the limited number of binding sites provided by the binding partner species present in the assay mixture.

Competitive binding-pair assays can be further differentiated as being homogeneous or heterogeneous in nature. In homogeneous assays, all of the reactants participating in the competition reaction are mixed together and the concentration of analyte is determined by its effect on the extent of binding between its binding partner and labeled analyte. The signal observed is a direct function of this binding and can be related to the overall concentration of analytes present in the test sample. U.S. Pat. No. 3,817,837, which is incorporated herein by reference, discloses a homogeneous, competitive immunometric assay in which the labeled analyte analog is a ligand-enzyme conjugate and the binding partner is an antibody capable of binding either the analyte or analyte analog. In general, homogeneous assay systems require both an external instrumentality to determine the result and the prior calibration of the observed signal by separate tests performed with known concentration of the specific analyte in a process known as standardization. While homogeneous assays have dominated competitive immunometric assay system development, such systems are not capable of providing results for the determination of multiple analytes in a test sample in a single-test format not requiring external instrumentality.

Heterogeneous, competitive binding-pair assays require separation of the bound, labeled analyte or its binding partner from the free, labeled analyte or its binding partner and a subsequent measurement of either the concentration of the bound or free fraction. Methodologies for performing these assays are described in U.S. Pat. Nos. 3,654,090, 4,298,685, and 4,506,009, which are incorporated herein by reference. The quantitative or semi-quantitative measurement of analyte concentration utilizing this methodology cannot be performed without the use of additional tests to calibrate the assay results. Hence, only the presence or absence of the analyte can be determined without additional instrumentation or tests. Recently, however, methods have been developed for the internal calibration of binding-pair assays by providing a device which incorporates reference zones whereby the given response at the reference zone represents the assay response for a specific concentration of the analyte. The response generated by the unknown concentration of the analyte in the test sample is then compared with the response at the reference zone to determine the concentration of the analyte in the test sample in a qualitative or quantitative manner. U.S. Pat. No. 4,540,659, which is incorporated herein by reference, describes the system that incorporates several analyte concentration standards. They provide the ability to make semi-quantitative determinations of analyte concentrations in competitive binding-pair assays through a direct visual examination.

Sample collection and application means are known within the relevant field. For example, an applicator component, consisting of a separate wand-like component with a bibulous material attached to one end, is described in U.S. Pat. Nos. 5,169,789 and 4,770,853, which are incorporated herein by reference. The sample is collected for assay by simple absorption of the aqueous sample and subsequent placement of the collection component into the assay device. U.S. Pat. No. 4,624,929, incorporated herein by reference, discloses a sample collector comprised of a bibulous membrane confined in a housing. Collection of the sample is facilitated by contacting the sample collector with the desired aqueous sample. European Patent Application Nos. 88303744.2 and 90301697.0, incorporated herein by reference, disclose a wick-like sample collector, comprised of bibulous material, which is contiguous with the internal chromatography material.

While there are numerous assay devices and sample collection and application means that are currently in use within the relevant fields, the device disclosed herein serves to mitigate several of the difficulties which are frequently encountered in the utilization of these devices. For example, the requirement for large initial sample volumes, sometimes as much as several milliliters, often becomes problematic with many commercially available devices. This volume requirement is a function of the comparatively inefficient sample collection and/or application means these devices possess. Moreover, the requirement for such large initial sample volumes can potentially lead to difficulties when only small sample volumes or only a single test sample is available.

In contrast, due to the utilization of a novel sample collector and applicator, the present invention requires comparatively small initial sample volumes for analysis of analyte concentration. The features of the present invention also negate the need for secondary, external sample collector/applicator, which many, if not all, of the currently utilized devices require. Furthermore, the present invention greatly reduces the probability of sample contamination or cross-contamination, which is frequently encountered with the use of such secondary means. An additional unique feature of the sample collector/applicator component of the present device is the ability to collect and solubilize a dried sample, which putatively contains the analyte, without the use of secondary instrumentalities or methodologies.

SUMMARY OF THE INVENTION

The present invention is directed to any type of binding-pair assay and device that utilizes chromatographic, capillarity-mediated transport for the qualitative or quantitative analysis of selected analytes in samples. The disclosed assay system is comprised of a chromatography device which incorporates a sample collection and application component for the delivery of the solubilized sample directly into the chromatographic flow. The disclosed device fulfills numerous, unmet needs within the relevant fields. It provides, but is not limited to, the following benefits:

(1) All required components of the assay system are contained within a single unitized device that is capable of being disassembled into a sample collector/applicator and detection means;

(2) the assay system allows the collection of the sample and its subsequent application to the chromatographic components in such a way as to minimize any potential sample diminution due to incomplete sample delivery;

(3) the assay system allows collection of a comparatively small sample volume;

(4) the assay system negates the requirement of an additional external instrumentality which collects and applies the sample to the assay device;

(5) the assay system minimizes the potential for sample contamination and/or cross-contamination caused by the use of non-integrated, external sample collection and/or application devices; and (6) one embodiment of the present assay system discloses the use of self-contained, breakable, reagent containers for the delivery of various solutions utilized in the analysis of the sample.

Currently, a major problem associated with binding-pair assays is the collection of the test sample and its subsequent application to the assay device. Many, if not all, of the commercially available devices require comparatively large sample volumes to be collected because the devices are inefficient in delivering the applied sample to the chromatographic means. The present device, however, greatly mitigates these difficulties via a novel sample applicator, which utilizes an absorbent wick-like component and air gap to facilitate sample delivery to the associated chromatographic components contained within the device. Therefore, the sample putatively containing the analyte of interest can be transferred to the chromatographic means by having the reagent(s) flow through the sample collector/applicator, concomitantly washing the sample onto the chromatographic means.

DESCRIPTION OF THE DRAWINGS

Those individuals skilled in the relevant art may better understand the present invention and appreciate its advantages by referring to the accompanying drawings wherein.

DETAILED DESCRIPTION OF THE INVENTION

Figure 1:
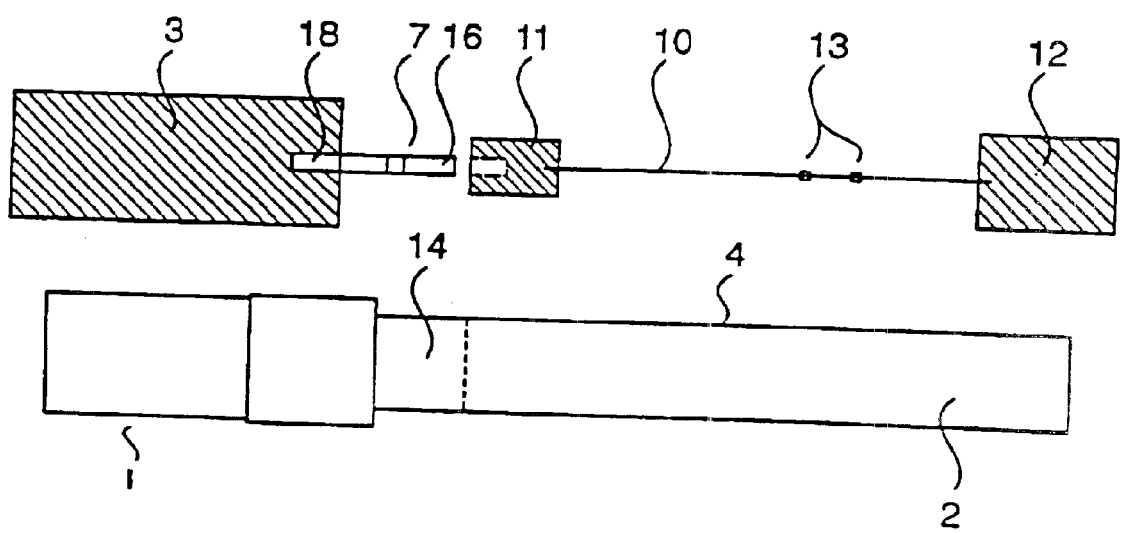
FIG. 1 shows a side view of the device detailing: the sampler member, the chromatography components, and the housing for said device.

The present invention provides binding-pair assays and devices that utilize capillarity-mediated, chromatographic transport, for the qualitative or quantitative analysis of selected analytes in samples. The invention is useful for a wide variety of assays, both ligand-based and non-ligand-based. Applicable ligand-based methodologies may include, but are not limited to, competitive immunoassays, non-competitive or so-called sandwich technique immunoassays, and blocking assays.

The use of the invention is not limited to immune systems. Other ligand assays include ligand-receptor assays, such as detecting insulin with an insulin receptor, and ligand-binding protein type assays, such as detecting certain antibiotics using a beta-lactam binding protein. Enzymes and their substrates can be determined as well. Applicable non-ligand-based assay methodologies may include any type of chemical and biochemical reactions that can be detected by a device that utilizes chromatographic, capillarity-mediated transport.

The present device comprises a housing which includes means for the collection of a sample putatively containing the analyte of interest, its application into the assay device and means for the detection, such as by direct visualization of the results of the binding-pair assay. The device may also further comprise (1) a housing with means enclosed therein for the conjugation of a label to a specific analyte to be detected within the sample (label transfer pad);

(2) a means for the sequestering the specific analyte within a defined spatial location (capture zone); and (3) a means for allowing liquids and any non-sequestered, solubilized materials contained therein, to undergo capillarity-mediated transport away from the capture location for subsequent absorption in a discrete area (blotter pad).

The present invention has broad application. It may also be employed in any number of assays which utilize bibulous material to mediate the flow away from an initial spatial location where the bibulous material is contacted with a medium putatively containing either the analyte to be determined or reagents used for the analysis of the analyte.

Prior to proceeding with the detailed description of the specific embodiments of the present invention, a number of terms will be defined.

Definitions

Analyte: the substance or composition to be measured in the assay.

Analyte analog: a specific derivative of the target analyte which may be optionally attached, either covalently or non-covalently, to other chemical species (e.g., a label). The analyte analog may be used, for example, to compete with the analogous target analyte for binding to the specific binding partner (i.e., competition assay). Where the modification of the analyte provides means to join the analyte analog to another molecule, or where the analyte has a functionality which is used to bind directly to another molecule, the analyte portion of the conjugate will be referred to as an analyte analog.

Binding partner: a molecule, such as a receptor, binding protein, antibody or antibody fragment, or enzyme (which binds to its substrate), which possesses the ability to interact with another molecule in a highly specific polar and spatial manner.

Antibody: an immunoglobulin, or a derivative or fragment thereof, which is capable of specifically binding to an antigen in a receptor-ligand based reaction. The antibody or fragment may be polyclonal or monoclonal, or native or chimeric. The preparation of antibodies is well known in the art. For example, antibodies may be generated by the immunization of a host followed by the collection of sera (polyclonal), or by hybridoma cell line-based technology (monoclonal).

Label: any molecule which is bound (via covalent or non-covalent means, alone or encapsulated) to another molecule or solid support and which is chosen for specific characteristics which allow detection of the labeled molecule. Generally, labels are comprised of, but are not limited to, the following types: particulate metal and metal-derivatives, radioisotopes, catalytic- or enzyme-based reactants, chromogenic substrates and chromophores, fluorescent and chemiluminescent molecules, and phosphors. The utilization of a label produces a signal which may be detected by means such as detection of electromagnetic radiation or direct visualization, and which can optionally be measured.

Bibulous material: a porous material that is susceptible to traversal by a liquid medium in response to capillary force. Such materials can be hydrophilic, or are capable of being rendered hydrophilic, and include natural polymeric substances (e.g., cellulosic materials), fiber-containing papers (e.g., filter and chromatographic papers), and synthetic or modified naturally-occurring polymers (e.g., nitrocellulose, cellulose acetate, polyacrylamide, cross-linked dextrose, or agarose), which are either utilized by themselves or in combination with other materials. The bibulous material may be poly-functional, or be capable for being made poly-functional, for example to permit covalent bonding of receptors, antibodies, or other compounds which function as components of the specific assay methodology.

Capillary Communicating Contact: When two elements of the device are in capillary communicating contact, the elements of the device are capable of transferring fluid from one element to the other, when fluid is present, by capillary action.

The Device

The present invention provides a methodology and device for any types of binding-pair assays, utilizing capillarity-mediated, chromatographic transport for the qualitative or quantitative analysis of a selected analyte putatively contained within a test sample.

FIGS. 1–6 depict a device for the detection of a specific analyte in a sample comprising two distinct components: the Sampler (1) and the Detection (2) members. The Sampler member (1) is comprised of an absorbent wick or tubing (6) which exhibits capillarity, and a reagent delivery system (22). The wick or tubing (6) is enclosed in a housing (4) fabricated from a rigid or semi-rigid, non-water-permeable material. When a wick is used for element 6, it is comprised of a bibulous material. When tubing is used for element 6, it may be capillary tubing of glass, plastic, or other appropriate material.

The reagent delivery system (22) can be contained within the housing (4), partially within and partially outside the housing (4), or fully outside the housing (4). Optionally, an absorbent reagent pad (3) is enclosed within the housing (4) as a part of the reagent delivery system (22). An opening, the reagent application port (5), can be optionally provided in the housing (4) of the Sampler member to facilitate the addition of various solutions through the reagent delivery system (22), optionally through the absorbent reagent pad (3).

The wick or tubing (6) is in capillary communicating contact with the reagent delivery system (22) via the absorbent reagent pad (3) when it is present, or via any other source of reagent. A line of demarcation (7) can be utilized on the absorbent wick or tubing (6) to facilitate the collection of a pre-determined volume of a liquid sample via capillary action.

The Detection member (2) is comprised of a housing, fabricated from a rigid or semi-rigid, non-liquid-permeable material, optionally providing an upper (8) and lower (9) section. The housing can serve to both contain and position various components of the assay device.

Contained within the housing is the chromatography region (24), utilizing a chromatography medium (10) which is comprised of at least a transit zone (20) and a capture zone (13). The transit zone (20) can optionally include a proximally located label transfer pad (11). When utilized, the label transfer pad (11) contains a labeled, specific, analyte-binding reagent (L-SABR) or the components and means for assembling an L-SABR (for a non-competitive reaction) or a labeled, specific, analyte analog (L-SAA) or the components and means for assembling an L-SAA (for a competitive reaction). If components and means for assembling the L-SABR or L-SAA are used, the components must be capable of assembling and interacting in the form of an L-SABR with the analyte, or in the form of an L-SAA with the binding partner. The L-SABR or L-SABR, or its components, is retained within the label transfer pad (11) while the absorbent material comprising the pad is in the dry state. When components and means for assembling an L-SABR or L-SAA are utilized, L-SABR or L-SAA is assembled prior to or when analyte moves through the transfer pad (11) during the course of the assay. The L-SABR or L-SAA (either initially present or subsequently assembled) becomes freely mobile through both the label transfer pad (11) (when used) and the porous chromatography medium (10) when contacted by the assay liquid.

Alternatively or additionally, label and/or components and means for assembling the L-SABR or L-SAA can be added through a detection port (19) which enables detection in the Detection member (2) optionally located at the proximal end of the transit zone (20). The L-SABR or L-SAA thus added or assembled enters the transit zone and becomes freely mobile through both the label transfer pad (11) (when used) and the porous chromatography medium (10) when contacted by a solution.

The detection port (19) can also be used for the addition of buffer(s), reagent(s) and/or other reaction components to be used in the assay. For example, a reagent useful in visualizing the L-SABR or L-SAA can be added through the detection port (19); likewise, a buffer for solubilizing L-SABR or L-SAA entrapped in the label transfer pad (11) can be added through the detection port (19).

The chromatography medium (10) can optionally be in capillary communicating contact with a distally located blotter pad (12). The chromatography medium (10) comprises a spatially-distinct location defined as the capture zone (13), said zone being located downstream from the transit zone (20) and the optional label transfer pad (11) and/or the optional detection port (19) and upstream from the blotter pad (12). A non-reagent-soluble, non-labeled specific analyte-binding reagent (SABR), or a specific analyte analog (SAA) is immobilized on the label transfer pad (11) when it is used. The L-SABR and the SABR can have the same or different reactive sites, depending on the type of assay to be performed. Likewise, the L-SAA and the SAA can have the same or different reactive sites.

In one possible embodiment, the assay of the sample putatively containing the analyte of interest is initiated by a separation of the Sampler (1) and Detection (2) members from one another. The distal end portion (16) of the absorbent wick or tubing (6) is next brought into contact with the chosen liquid sample (e.g., a blood droplet). The sample is drawn into the absorbent wick or tubing (6), via capillary action, until such time as the desired amount of sample has been collected (for example, until the level of the collected liquid sample has reached the line of demarcation (7)).

Figure 6:
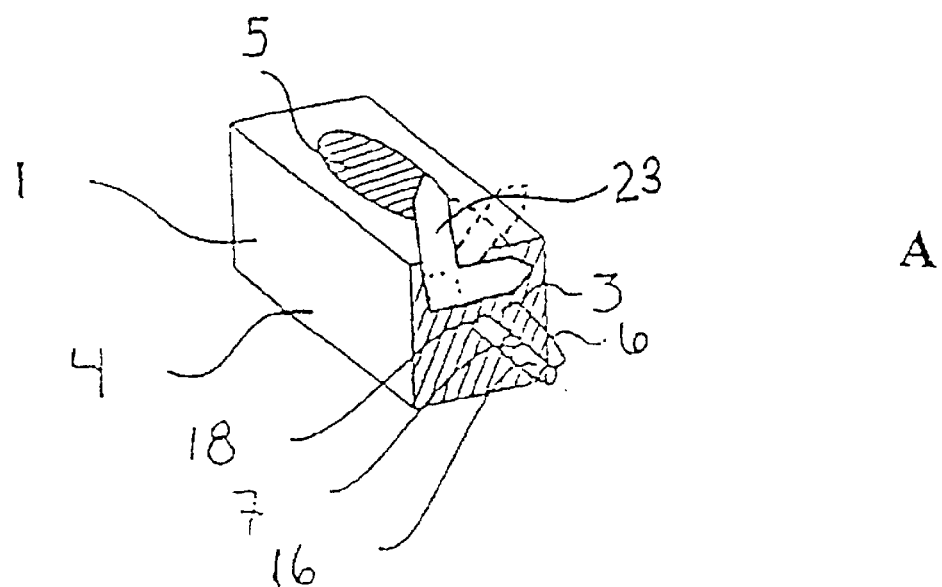
FIG. 6 shows the sampler member with an optional "sharp" for drawing blood or other body fluids.
Figure 6:
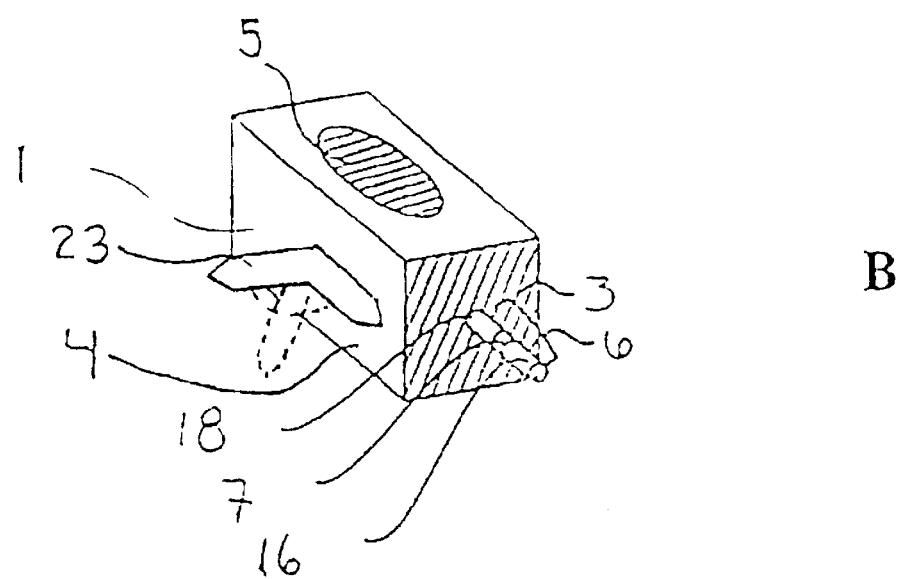

Optionally, a mechanism capable of puncturing skin to draw blood or other fluids (a "sharp") (23) can be incorporated in the device. Preferably this sharp is retractable or can be easily removed from the sampler member (1) after puncture. FIG. 6 shows two versions of a retractable sharp. In another embodiment, illustrated in FIG. 7, the sharp can itself be concave or hollow and can surround the wick or tubing (6). The sample can then flow along the sharp body and be exposed to the distal end of the wick or tubing (6) to allow collection of the sample by the wick or tubing (6). Alternatively, the concave or hollow sharp can be positioned next to the wick or tubing (6) such that the sample will flow along the sharp body and then encounter the proximal end of the wick or tubing (6) at the base of the sharp, such as through a hole in the sharp. The sample would then proceed to flow through the wick or tubing (6).

The assay device is then reassembled by the insertion of the Sampler member (1) into the Detection member (2), such that the absorbent wick or tubing (6) is placed in capillary communicating contact with the chromatography medium (10) present at the proximal end of the label transfer pad (11). A solution (e.g., buffer) is then added to the reagent application port (5) such that the absorbent reagent pad (3) becomes saturated. The solution is drawn into the absorbent wick or tubing (6) by its inherent capillarity, causing the movement of the test sample through the absorbent wick or tubing (6) and into the label transfer pad (11).

An air gap (14) is utilized to separate the absorbent reagent pad (3) from the label transfer pad (11), with the air gap (14) being "bridged" by the absorbent wick or tubing (6) upon reassembly of the assay device. The utilization of the air gap (14) maximizes the transfer of the liquid sample contained within the absorbent wick or tubing (6) to the label transfer pad (11). It forces capillarity-mediated transfer of the liquid from the absorbent reagent pad (3) through the absorbent wick or tubing (6), concomitantly facilitating sample transfer.

In this embodiment, the movement of the test sample and liquid reagent into the label transfer pad (11) causes the L-SABR or L-SAA to be solubilized, thus facilitating the formation of a complex between this labeled moiety and any specific analyte putatively contained within the test sample.

When L-SABR is used, the analyte/L-SABR complex subsequently interacts with, and is sequestered by, the immobilized, non-labeled SABR located within the capture zone (13). Depending upon the type of label chosen, detection of this sequestered complex may be accomplished by direct visualization via the transparent viewing port (15) located within the upper section (8) of the Detection member (2) over capture zone (13) to allow visualization of the capture zone (13).

Any dissolved, non-complex and non-sequestered materials found within the capture zone can be minimized by a continuous, capillary-based flow of the solution (e.g., buffer) applied to the absorbent reagent pad (3) which washes these non-sequestered components past the capture zone (13). Generally, this flow will continue until either the absorbent reagent pad is depleted or the blotter pad (12) becomes saturated.

Figure 4:
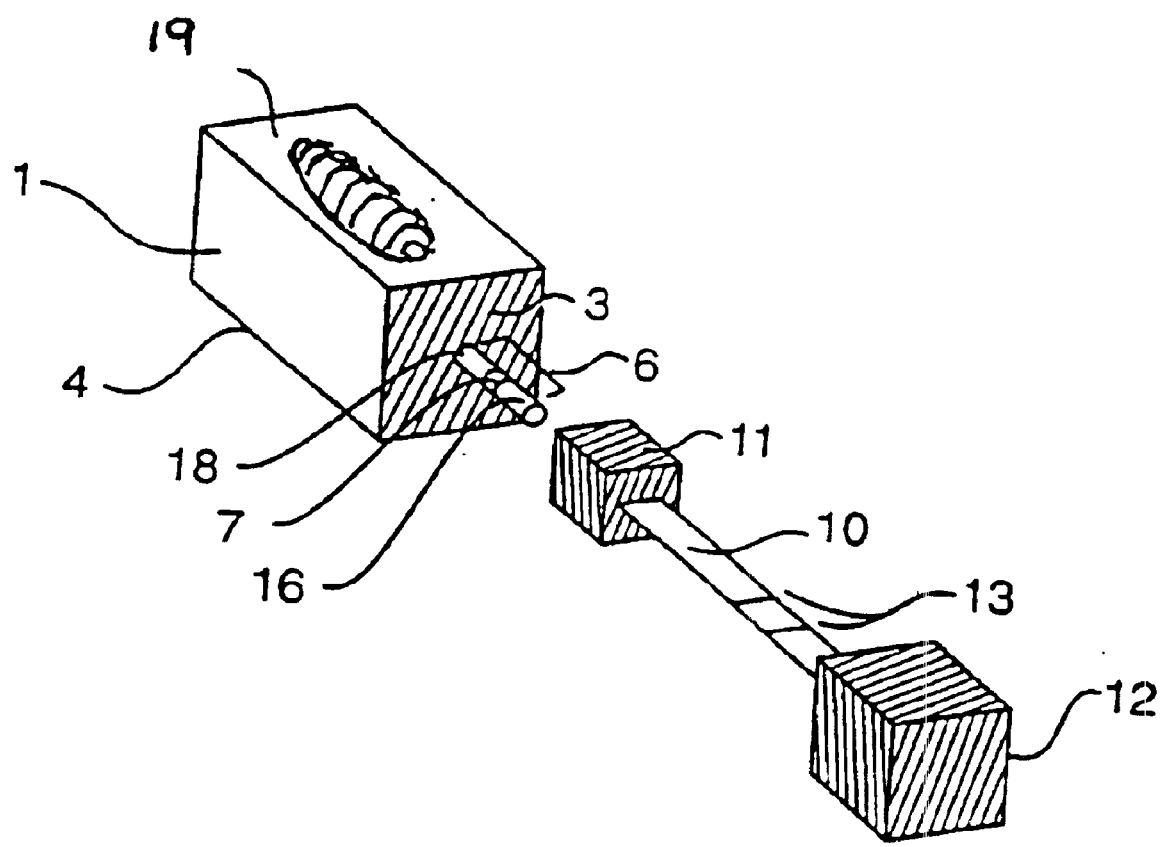
FIG. 4 shows an orthographic view detailing the reagent containers. There may be one or more of these containers associated with the device, depending upon the nature of the assay being performed.
Figure 5:
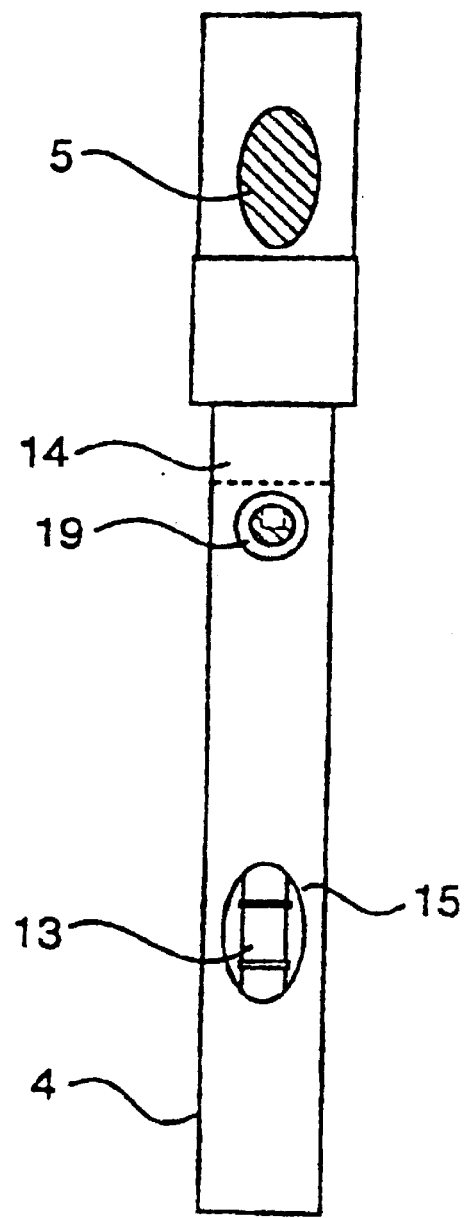
FIG. 5 shows an orthographic view with the additional detection port.

In another embodiment, illustrated in FIG. 4, the device incorporates one or more self-contained, breakable reagent container(s) (17). The reagent container (17) encloses a solution which, when released, flows into and/or through the absorbent reagent pad (3). This solution may optionally contain a variety of substances including, but not limited to, analyte, analyte analog, specific analyte -binding reagent, signal generating reagent (e.g., a substrate for an enzymatic label), or any other ancillary reagent. The container may be integral with the housing of the device, separate therefrom, or both, where more than a single self-contained reagent container is employed.

The device may optionally comprise a reagent application port (5), so that at least one of the breakable containers may be positioned so as to allow fluid flow through the reagent application port (5) upon rupture of the container(s) (17). Upon rupture, the enclosed solution is rendered capable of undergoing capillarity-mediated transport through the optional absorbent reagent pad (3) and the absorbent wick or tubing (6).

The reagent containers (17) themselves are preferably water-impermeable before breakage, and may be rigid, semi-rigid, or flexible. The solution contained therein is capable of being delivered to the assay device by crushing, cutting, puncturing, melting, or otherwise rupturing the container (17) or a seal between the container and the assay device. Materials utilized in the fabrication of the reagent containers may include, but are not limited to, glass, polymers, fiber-reinforced papers, plastics, waxes, and other materials which meet the previously discussed structural criteria. The container shape may be any shape which is spatially and sterically compatible with the present device (e.g., spherical, rectangular, ellipsoidal, and so-forth). The total volume of the reagent container (17) will vary, depending upon the specific liquid reagent contained therein, the function of the given reagent in the assay, the overall size of the assay device, the total absorptive capacity of the bibulous materials utilized in the assay device, the total number of reagent containers employed, and similar limitations.

The housing comprising either or both the Sampler (1) and Detection (2) components of the assay device may be fabricated from various moisture-impermeable materials including, but not limited to, thermo- and vacuum-formed plastics, fiber-reinforced paper products, polymers and other appropriate materials. The material utilized to fabricate the housing preferably does not interfere with the sample, the sample medium, or any reagents used in the assay procedure. While a transparent material can be used in the fabrication of the viewing port (15), alternative embodiments include no covering on the viewing port (15), or a large portion of the upper section (8) of the Detection component (2) being fabricated from transparent material.

Following the insertion of the various chromatographic materials during the construction of the device, the upper (8) and lower (9) sections of the Detection component (2) may be securely fastened together by ultrasonic welding, adhesives, and other relevant methodologies. Alternately, the Sampler (1) and/or the Detection (2) components may each be fabricated in a single, unitized piece, which is subsequently used to enclose the various internal components.

Both the absorbent reagent pad (3) and blotter pad (12) may be constructed from any bibulous, porous, or fibrous material that is capable of absorbing a liquid. Examples include porous plastic polymer materials including, but not limited to, polypropylene, high molecular weight polyethylene, polyvinylidene fluoride, acrylonitrile, and polyterafluoroethylene; cellulosic materials (e.g., nitrocellulose); or heavy-weight, high-absorbency chromatographic paper. The use of a chromatographic paper in the fabrication of the blotter pad (12) is generally preferable, due to its high degree of absorbency and low cost. Additionally, with respect to the absorbent reagent pad (3), it is preferred that the chosen material retains some degree of structural integrity when saturated. Regardless of the material chosen, it may be advantageous to pre-treat the member with a surface-active agent during fabrication so as to reduce any inherent hydrophobicity and concomitantly increase its ability to absorb and deliver liquid samples in an efficacious manner.

It should also be noted that the proximal end (16) of the absorbent wick or tubing (6) member may be saturated with an inert dye (e.g., Blue Dextran) to facilitate the visualization of the chromatographic flow of colorless solutions.

Chromatographic media (10) which may be utilized with the present device include those chromatographic substrate materials possessing capillarity and the capacity for chromatographic solvent transport of non-immobilized, liquid-soluble reagents and sample components. While a wide variety of chromatographic materials used for paper chromatography are suitable for use with this invention, the use of microporous or microgranular thin-layer chromatographic substrates is generally preferred due to the marked increase in speed and resolution which these materials provide.

The chromatographic material is preferably inert, as well as physically and chemically non-reactive with any of the sample components, reagents, or reaction products. Preferably, microporous nitrocellulose material may be utilized with a high degree of efficacy in the disclosed device. Nitrocellulose has the added advantage that the specific analyte-binding reagent (e.g., antibody) present in the capture zone may be immobilized without prior chemical treatment.

In contrast, if the chromatography material is comprised of a chromatographic paper, for example, the immobilization of the specific analyte-binding reagent can be performed via chemical coupling methodologies. Commonly used reagents include, but are not limited to, cyanogen bromide (CnBr), carbonyldiimididazole, or tresyl chloride. Additionally, reagents capable of blocking non-specific binding sites on the chromatographic medium which might hinder chromatographic solvent transport of the liquid sample or reagents may also be employed in the fabrication of the present device. Commonly used reagents include, but are not limited to, bovine serum albumin (BSA), gelatin, and casein, which are preferably selected for their ability to not interfere with, or cross-react with, the sample components, reagents, or reaction products.

SABR which may be utilized with the present invention are readily identifiable to one of skill in the relevant art and include those materials which are members of a "specific binding pair" (e.g., ligand and receptor, antigen and antibody, or enzyme and substrate). For example, an analyte and a receptor are related in that the receptor specifically binds to the analyte and possesses the capacity to differentiate the analyte from other materials having similar characteristics. The methodologies and devices disclosed by the present invention are particularly useful in the practice of immunological assay techniques wherein the specific analyte-binding reagents consist of receptors, antibodies, antibody fragments, or synthetic antibodies or antigens. The present device preferably employs a specific binding pair consisting of the desired analyte and an antibody which is specific for, i.e., has a high affinity for binding to, said analyte.

The "label" utilized on the L-SABR or L-SAA disclosed in the present invention may be selected from, but is not limited to, the following categories: chromogens/fluorescers, particulate metals or their derivatives, components of catalyzed or enzymatic reactions, chemiluminescent compounds, and radioactive isotopic labels.

Chromogens include those compounds which absorb light in a distinctive range such that a specific color may be visibly observed (i.e., dyes), or emit light when irradiated with electromagnetic radiation of a specific wavelength or wavelength range (i.e., fluorescent compounds). Illustrative dye types include, but are not limited to, quinoline, acridine, alizarin, cyanine and anthraquinoid dyes. Fluorescent compound functional groups include, but are not limited to, porphyrins, 2-aminoaphthalene, p,p'-diaminobenzophenone imines, 1,2-benzophenazin, and quaternary phenanthridine salts. By irradiating a fluorescer with light of a specific wavelength, one may obtain a plurality of emissions, thus providing multiple measurable events.

Particulate metal sol-based label can be obtained by the direct or indirect coupling of the desired reaction component (e.g., antibody) with particles of an aqueous dispersion of a metal, metal compound, or polymer nuclei coated with a metal or metal compound, having a particle size of at-least 5 nm. The term "coupling" is understood within the relevant art to encompass any type of chemical or physical binding, and includes covalent and hydrogen bonds, polar attraction, absorption, and adsorption. Metals utilized in this labeling methodology may include, but are not limited to gold, platinum, silver, copper, and iron. A metal sol is generally defined as a suspension of metal or metal-derivative particles which, due to their extremely small diameter, remain in a suspension solely because of the Brownian motion effects. The particulate metal sols to be used as labels may be prepared in a number of ways which are in themselves known. For example, the preparation of a gold sol has been described (G. Frens, 241 *Natural Physical Science* 20 (1973)), which is incorporated herein by reference.

Catalyzed reactions may be either enzyme or non-enzyme based. Considerations which must be taken into account when using an enzyme-based label include, but are not limited to, enzyme stability, turnover rate, sensitivity of the reaction to environmental factors, the nature of the substrate and products, and the effect of conjugation on the enzyme's catalytic properties. The methodologies involved in enzymatic labeling are well known within the relevant art. A preferred example is horseradish peroxidase (HRPO), used in conjunction with 1.7-dihydroxynaphthalene, and 4-amino-antipyrine hydrochloride.

An alternative form of labeling is the use of chemiluminescent compounds. The chemiluminescent source comprises a compound that becomes electronically excited following a chemical reaction and subsequently may either emit light in the visible range or donate energy to a secondary fluorescent acceptor compound. These include, but are not limited to, the 2.3-dihydro-1,4-phthaiazinedione family (luminol), the 2,4,5-triphenylimidazole family (lophine), and the para-dimethylamino oxalate-ester family (luciferase).

Radioisotopic labels are widely utilized in immunometric assays. The radiolabel may be selected from, but is not limited to, the following radioactive isotopes: $^{3}H$, $^{14}C$, $^{32}P$, $^{125}I$ and $^{131}I$. Methods of labeling substances with radioactive labels are well known within the relevant art.

In the present invention, the utilization of metal sol-based labels is preferred. For example, a gold sol label conjugated to the specific analyte-binding reagent (e.g., antibody) may be utilized. This label allows the end-point of the reaction to be visualized without the need for any additional instrumentality.

The present invention clearly fulfills several unfulfilled needs within the field of binding-pair assays. The novel construction of the unitized Sampler member facilitates both the initial collection, and subsequent assay of the sample putatively containing the analyte. The utilization of a novel absorbent wick/air gap feature in the Sampler component not only minimizes the potential for the contamination and cross-contamination of the sample by not requiring a secondary external means for sample collection (e.g., via syringe, pipette, capillary tube, etc.), but also maximizes the transfer of the sample to the assay device, thus minimizing the required sample volume.

The following specific embodiments, by-way of example, are descriptions of the utilization of the disclosed invention for the purpose of immunometric determination of a specific analyte present in a sample. These examples are not meant to limit the scope of the present invention in any manner, but instead, merely serve to illustrate some of many possible embodiments.

EXAMPLE 1

Figure 2:
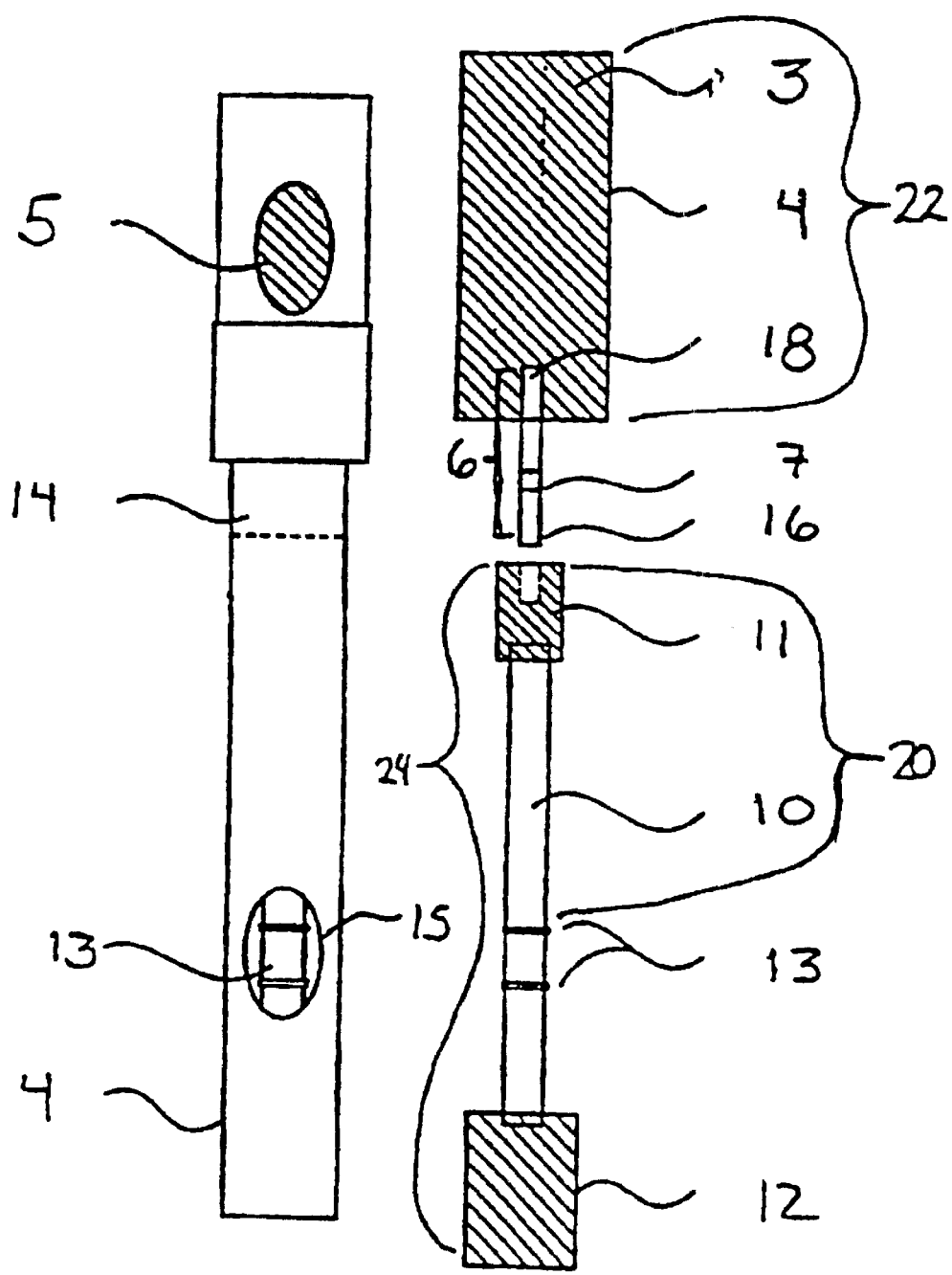
FIG. 2 shows a top view of the device detailing: the sampler member, the chromatography components, and the housing for said device.
Figure 3:
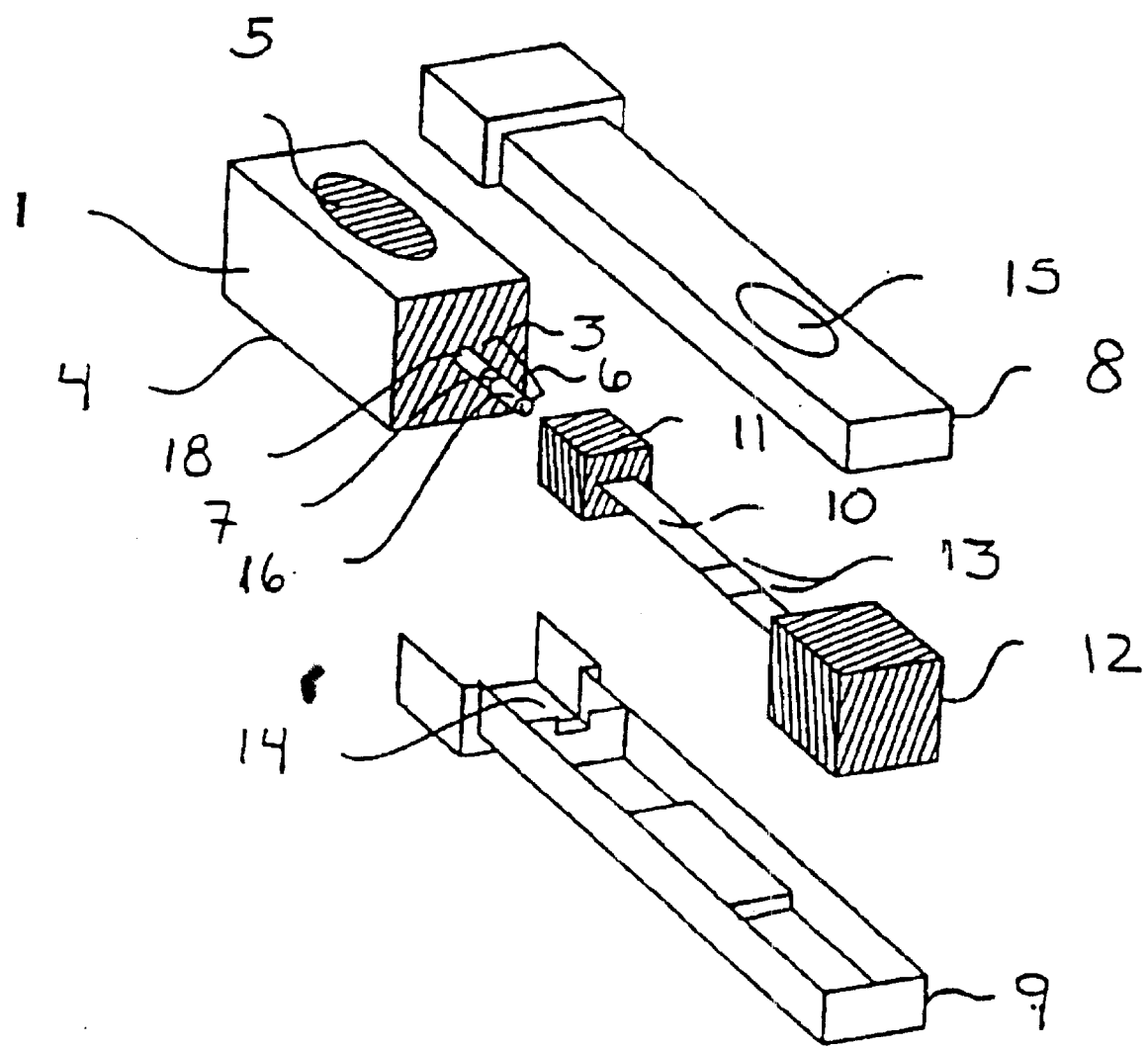
FIG. 3 shows an orthographic view detailing the sampler member, the chromatography components, and an "exploded" illustration of the housing for the device.

With reference to FIGS. 1–3, the assay is begun by a separation of the Sampler (1) and Detection (2) components from one another. The distal end (16) of the absorbent wick (6) is next brought into contact with the sample, a blood droplet. The sample is then drawn into the absorbent wick (6) via capillarity-mediated transfer until such time as the fluid level has reached the line of demarcation (7), thus providing a means for the collection of a pre-determined sample volume. The assay device is then reassembled by the insertion of the Sampler component (1) into the Detection component (2), such that the absorbent wick (6) is placed in capillary communicating contact with the label transfer pad (11). A solution is then added to the reagent application port (5) such that the absorbent reagent pad (3) is saturated. The solution is subsequently drawn into the absorbent wick (6) by its inherent capillarity, thus causing the movement of the sample through the absorbent wick (6) and into the label transfer pad (11). The label transfer pad (11) contains a particulate metal label which is conjugated to an antibody, with the antibody being specific for the analyte putatively contained within the test sample. The particulate metal label/antibody conjugate ("labeled antibody") is found in a dried, non-immobilized form within the label transfer pad (11). An air gap (14) is utilized to separate the absorbent reagent pad (3) from the label transfer pad (11), and is bridged by the absorbent wick (6) upon reassembly of the assay device. The concomitant movement of the test sample and solution into the label transfer pad (11) causes the labeled antibody to be solubilized, facilitating the formation of a complex between the labeled antibody and any specific analyte putatively contained within the test sample. The analyte/labeled antibody complex subsequently interacts with, and is sequestered by, the immobilized, non-labeled antibody located within the capture zone (13). Detection of this sequestered complex is visualized via a transparent viewing port (15) located within the upper section (8) of the Detection component (2) and over the capture zone (13). Any liquid soluble, non-reacting materials found within the capture zone (13) are minimized by a continuous, capillary-based flow of the solution initially applied to the absorbent reagent pad (3). This flow continues until either the absorbent reagent pad (3) is depleted of solution or the blotter pad (12) becomes saturated.

EXAMPLE 2

With reference to FIGS. 1–3, the device is utilized as in Example 1 with the exception that the labeled antibody has been localized to the distal end-portion (16) of the absorbent wick (6) rather than to the label transfer pad (11). This specific embodiment allows for the pre-incubation of the sample with the labeled antibody prior to both the reassembly of the Sample (1) and Detection (2) components and the subsequent addition of a solution (e.g., buffer) to the reagent application port (5). This specific embodiment ensures that the labeled antibody reaches the test sample, by the process of diffusion, in gradually decreasing concentrations, due to the solubilizing of the labeled antibody following the addition of a solution (e.g., buffer) to the reagent application port (5). The timing between the initial collection of the test sample and the subsequent reassembly/solution addition may be varied to allow for the adjustment of assay sensitivity.

EXAMPLE 3

With reference to FIGS. 1–3, the device is utilized as in Example 1 with the exception that the labeled antibody has been localized to the proximal end-portion (18) of the absorbent wick (6) rather than to the label transfer pad (11). This specific embodiment ensures that the labeled antibody reaches the test sample, by the process of diffusion, in gradually increasing concentrations, as opposed to the previous example (Example 2) where the labeled antibody reaches the test sample in gradually decreasing concentrations, due to the solubilizing of the labeled antibody following the addition of a solution (e.g., buffer) to the reagent application port (5). Requirements for differing reaction kinetics may favor one embodiment over the other.

EXAMPLE 4

With reference to FIGS. 1–3, the device is utilized as in Example 1 with the additional step of localizing a chromogenic compound (e.g., liquid-soluble dye) to the distal end-portion (16) of the absorbent wick (6). This specific embodiment allows for the direct visualization of capillarity-mediated transfer of the test sample through the chromatography medium (10), thus facilitating monitoring of difficult-to-detect samples (e.g., colorless aqueous samples or various physiological fluids).

EXAMPLE 5

With reference to FIGS. 1–3, the device is utilized as in Example 1 with the exception that following the initial disassembly of the assay device by the removal of the Sampler component (1) from the Detection component (2), and prior to the actual collection of the test sample, a solution (e.g., buffer) is added to the reagent application port (5). This causes the saturation of the absorbent wick (6) member and allows for the solubilizing and capillarity-mediated transfer of a dried or semi-dried sample onto the distal end-portion (16) of the absorbent wick (6).

EXAMPLE 6

With reference to FIGS. 1–3, the device is utilized as in Example 1 with the exception that after the actual collection of the test sample, a solution with an added reagent such as analyte or analyte analog is added to the reagent application port (5). This causes the saturation of the absorbent wick (6) member and allows for the solubilizing and capillarity-mediated transfer of a dried or semi-dried sample onto the distal end-portion (16) of the absorbent wick (6).

EXAMPLE 7

With reference to FIGS. 1–4, the device is utilized in a manner so as to provide a competitive immunoassay. The competitive assay may be homogeneous or heterogeneous in nature. In a homogeneous assay, all of the reactants participating in the competition reaction are mixed together and the concentration of the analyte is determined by its effect on the extent of binding between the receptor and labeled analyte analog. The observed signal is a direct function of this binding and can be related to the overall concentration of analyte present in the test sample.

In a heterogeneous competitive binding-pair assay the bound, labeled analyte or receptor is separate from the free, labeled analyte or receptor. The concentration of the bound or free fraction is subsequently measured.

In this example, the analyte analog may be added to the device by direct application to the reagent application port (5) using an external delivery device, or, alternately, it may be contained within the reagent containers (17) which, when ruptured, deliver the analyte analog to the device. The analyte analog may be delivered to the device either before or after the actual collection of the test sample. Alternatively, it may be contained in the wick or tubing (6).

EXAMPLE 8

In addition to ligand-based assays, this type of device is also useful for non-ligand assay methodologies such as to quantify blood glucose in diabetes. With reference to FIGS. 1–3, the device is utilized as in Example 4. Test sample potentially containing β-D glucose is assayed, and glucose oxidase is the solution added to the reagent application port (5). Glucose oxidase reacts with β-D glucose in the presence of oxygen to produce D-glucose acid and $H_2O_2$. Subsequently, horseradish peroxidase (HRPO), 1,7-dihydroxynaphthalene, and 4-aminoantipyrine hydrochloride are added to the distal end-portion (16) of the absorbent wick (6) as chromogenic compounds. Alternatively, the compounds can be added before or during the assay through the detection port (19) to have the HRPO system present on the label transfer pad (11), or can be located directly on (a)

the label transfer pad (11), (b) the chromatography medium (10), or (c) the capture zone (13).

EXAMPLE 9

This device can also be used to puncture skin to draw blood or other fluids for the assay to be run in the device. With reference to FIGS. 6A and 6B, the retractable sharp (23) is extended. used to perforate the skin, and is then either retracted or broken off and disposed of. The sample is then collected and assayed as described in the previous examples.

EXAMPLE 10

Figure 7:
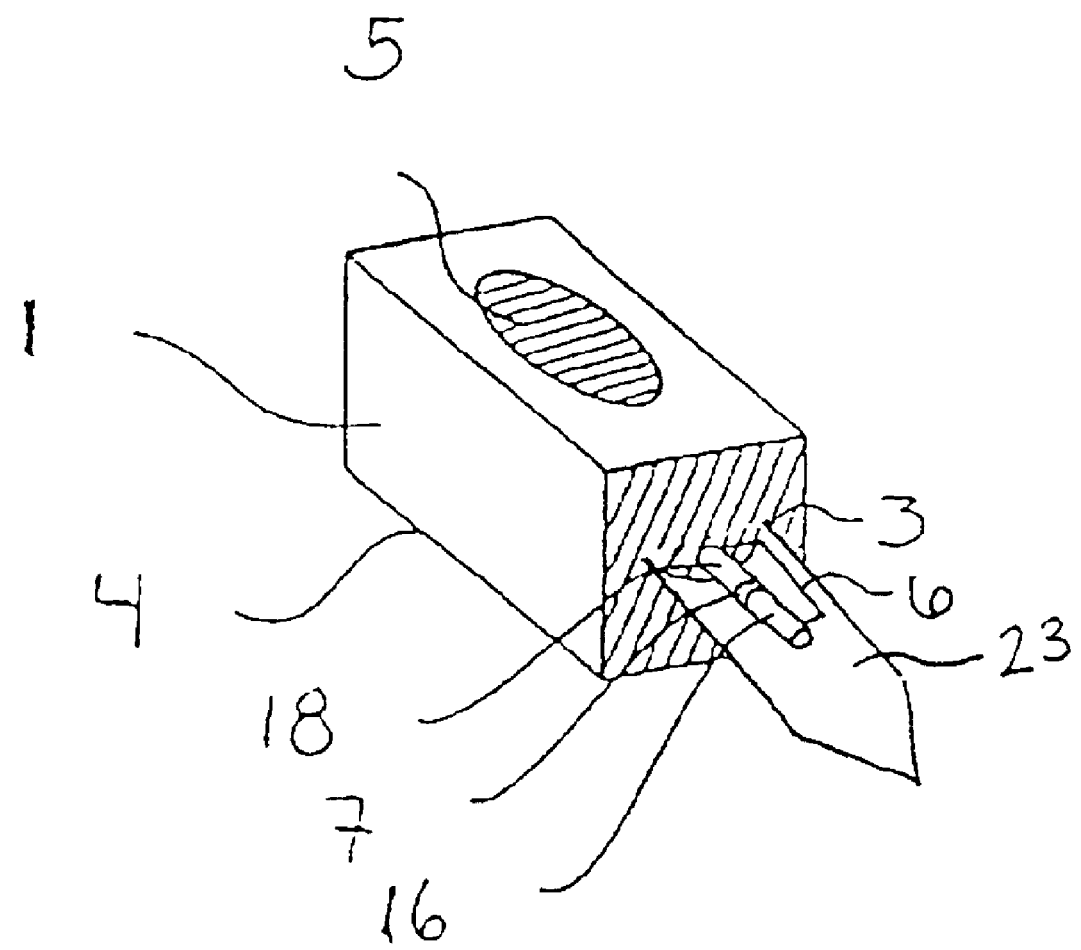
FIG. 7 shows the sampler with a sharp surrounding the absorbent wick or tubing.

In another embodiment of the device, as illustrated in FIG. 7, the sharp (23), which is concave or a hollow tube, is used to perforate the skin. The sample then flows through the sharp to the wick or tubing (6). The sample is then assayed as described in the previous examples.

While embodiments and applications of the present invention have been described in some detail by way of illustration and example for purposes of clarity and understanding, it would be apparent to those individuals skilled within the relevant art that many additional modifications would be possible without departing from the inventive concepts contained herein.

What is claimed is:

1. A device for performing a binding pair assay comprising:
    (a) a housing comprising a sampler member and a detection member, wherein the device is capable of being separated into at least two parts comprising the sampler member and the detection member, and the device is further capable of being assembled into one part;
    (b) a chromatography region associated with the detection member comprising a chromatography medium having a transit zone and a capture zone;
    (c) a sample collector associated with the sampler member that is exposed to receive sample upon separation of the device into the sampler member and the detection member, and wherein the sample collector is in capillary communicating contact with the capture zone through the transit zone when the device is assembled and;
    (d) a reagent delivery system positioned relative to the sampler member for delivering a liquid reagent to the sample collector, wherein the reagent delivery system is positioned so that the liquid regent is added to the reagent delivery system after the sampler member and detection member are assembled into one part and flows through the sample collector and into the chromatography region.

2. The device of claim 1 wherein the sample collector comprises an absorbent wick or tubing.

3. The device of claim 2 wherein the absorbent wick comprises a bibulous material.

4. The device of claim 2 wherein the bibulous material is selected from the group consisting of filter paper, chromatographic paper, nitrocellulose, cellulose acetate, polyacrylamide, cross-linked dextrose, and agarose.

5. The device of claim 2 wherein the absorbent wick or tubing comprises at least one volume indicator near the distal end to indicate sample volume.

6. The device of claim 2 wherein the sample collector is located in the sampler member.

7. The device of claim 1 wherein the reagent delivery system comprises an absorbent reagent pad.

8. The device of claim 7 wherein the reagent delivery system is positioned upstream of the sample collector.

9. The device of claim 7 wherein the sample collector comprises an absorbent wick or tubing and conducts liquid reagent from the reagent delivery system to the transit zone when the device is assembled.

10. The device of claim 7 wherein the reagent delivery system comprises a breakable reagent container that delivers reagent to the end of the sample collector that is in contact with the reagent delivery system, when the container is broken.

11. The device of claim 10 wherein the reagent delivery system comprises a reagent application port positioned to allow introduction of liquid reagent at the distal end of the sample collector.

12. The device of claim 7, wherein the sampler member further comprises a sharp for perforating skin to draw blood or other fluids to be used as the sample.

13. The device of claim 12 wherein the sharp is positioned to allow sample to flow along the sharp to the absorbent wick or tubing.

14. The device of claim 7 wherein the transit zone comprises a bibulous material and further comprises a label transfer pad.

15. The device of claim 14 wherein the label transfer pad is located at the end of the transit zone that is opposite of the capture zone.

16. The device of claim 14 wherein the label transfer pad contains labeled moieties selected from (a) a labeled specific analyte-binding reagent, (b) a labeled analyte analog, (c) components and means for producing within the label transfer pad a labeled specific analyte-binding reagent, or (d) components and means for producing within the label transfer pad a labeled specific analyte analog.

17. The device of claim 16 wherein the means for producing a labeled specific analyte-binding reagent or a labeled specific analyte analog include a detection port adjacent to the label transfer pad positioned to allow the addition of elements required to assemble the labeled specific analyte-binding reagent or labeled specific analyte analog.

18. The device of claim 17 wherein the sample collector is positioned to allow capillary communicating contact with the label transfer pad when the housing is assembled.

19. The device of claim 18 wherein the labeled moieties are distributed on the label transfer pad so that the labeled specific analyte-binding reagent or labeled specific analyte analog becomes mobile upon fluid contact between the sample collector and the label transfer pad.

20. The device of claim 18 wherein the labeled moieties are labeled with one or more labels selected from the group consisting of a radioisotope, a particulate metal, a dye, one or more components of a catalyzed or enzymatic reaction, and a chemiluminescent compound.

21. The device of claim 7 wherein the simple collector comprises labeled moieties selected from (a) a labeled specific analyte-binding reagent, and (b) a labeled analyte analog.

22. The device of claim 21 wherein the labeled moieties are present at or near the end of the sample collector that is opposite of the end of the sample collector that is in capillary communicating contact with the capture zone through the transit zone when the device is assembled.

23. The device of claim 21 wherein the labeled moieties are present at or near the end of the sample collector that is in capillary communicating contact with the capture zone through the transit zone when the device is assembled.

24. The device of claim 22 wherein the labeled moieties are labeled with one or more labels selected from the group consisting of a radioisotope, a particulate metal, a dye, one or more components of a catalyzed or enzymatic reaction, and a chemiluminescent compound.

25. The device of claim 7 wherein the reagent delivery system is comprised of a reagent application port.

26. The device of claim 25 wherein the reagent application port is positioned to allow introduction of liquid reagent at the end of the sample collector that is in capillary communicating contact with the capture zone through the transit zone when the device is assembled.

27. The device of claim 26 wherein the liquid reagent contains a substance selected from the group consisting of an analyte, an analyte analog, a specific analyte-binding reagent, a signal-generating reagent and an ancillary reagent.

28. The device of claim 7 wherein the reagent delivery system comprises an absorbent reagent pad.

29. The device of claim 28 wherein the reagent delivery system further comprises at least one breakable reagent container and the absorbent reagent pad is positioned between at least one breakable reagent container and the sample collector.

30. The device of claim 29 wherein the absorbent reagent pad is in capillary communicating contact with the sample collector.

31. The device of claim 7 further comprising a detection port positioned adjacent to the end of the chromatography region that makes contact with the sampler member when the device is assembled and shaped to allow addition of reagent to the chromatography region.

32. The device of claim 31 wherein the detection port is positioned adjacent to the transit zone.

33. The device of claim 7 further comprising an air gap between the reagent delivery system and the chromatography region, the air gap positioned so that the sample collector bridges the air gap and creates capillary communicating contact between the reagent delivery system and the chromatography region.

* * * * *